(12) United States Patent
Yokota et al.

(10) Patent No.: US 12,351,765 B2
(45) Date of Patent: Jul. 8, 2025

(54) SATURATED ALIPHATIC HYDROCARBON COMPOUND COMPOSITION, LUBRICANT COMPOSITION, AND METHOD FOR PRODUCING SATURATED ALIPHATIC HYDROCARBON COMPOUND COMPOSITION

(71) Applicant: IDEMITSU KOSAN CO., LTD., Chiyoda-ku (JP)

(72) Inventors: Kiyohiko Yokota, Ichihara (JP); Kiyokazu Katayama, Ichihara (JP); Kanako Samejima, Ichihara (JP); Narinobu Kagami, Chiba (JP); Kouta Oba, Chiba (JP); Naoyuki Ueda, Chiba (JP); Takahiro Sakaguchi, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 443 days.

(21) Appl. No.: 17/629,173

(22) PCT Filed: Jul. 20, 2020

(86) PCT No.: PCT/JP2020/028118
§ 371 (c)(1),
(2) Date: Jan. 21, 2022

(87) PCT Pub. No.: WO2021/015172
PCT Pub. Date: Jan. 28, 2021

(65) Prior Publication Data
US 2022/0251461 A1   Aug. 11, 2022

(30) Foreign Application Priority Data
Jul. 25, 2019 (JP) .................. 2019-137092

(51) Int. Cl.
| C10G 69/12 | (2006.01) |
| C10M 105/04 | (2006.01) |
| C10M 171/02 | (2006.01) |
| C10N 30/00 | (2006.01) |
| C10N 30/02 | (2006.01) |

(52) U.S. Cl.
CPC ......... *C10G 69/126* (2013.01); *C10M 105/04* (2013.01); *C10M 171/02* (2013.01); *C10G 2300/1062* (2013.01); *C10G 2300/1088* (2013.01); *C10G 2300/302* (2013.01); *C10G 2300/304* (2013.01); *C10M 2203/022* (2013.01); *C10N 2030/02* (2013.01); *C10N 2030/74* (2020.05)

(58) Field of Classification Search
CPC .......... C10G 69/126; C10G 2300/1062; C10G 2300/1088; C10G 2300/302; C10G 2300/304; C10G 2400/10; C10G 45/60; C10G 50/02; C10M 105/04; C10M 171/02; C10M 2203/0206; C10M 2203/022; C10M 107/02; C10M 107/10; C10M 2205/0285; C10N 2030/02; C10N 2030/08; C10N 2030/72; C10N 2030/74; C10N 2020/011; C10N 2020/02; C10N 2060/02; C10N 2070/00; C07C 2/30; C07C 5/03; C07C 5/2575; C07C 7/04; C07C 2531/14

See application file for complete search history.

(56) References Cited

U.S. PATENT DOCUMENTS

| 4,282,392 | A | 8/1981 | Cupples et al. |
| 5,728,907 | A | 3/1998 | Squicciarini et al. |
| 6,824,671 | B2 * | 11/2004 | Goze .................. C10M 109/02 208/19 |
| 2002/0193650 | A1 | 12/2002 | Goze et al. |
| 2004/0082728 | A1 | 4/2004 | Wu et al. |
| 2005/0045527 | A1 | 3/2005 | Goze et al. |
| 2006/0116498 | A1 | 6/2006 | Wu et al. |
| 2007/0123659 | A1 | 5/2007 | Wu et al. |
| 2008/0146469 | A1 | 6/2008 | Sato et al. |
| 2011/0178348 | A1 | 7/2011 | Heilman et al. |
| 2014/0323665 | A1 | 10/2014 | Wu et al. |

(Continued)

FOREIGN PATENT DOCUMENTS

| CN | 106414680 A | 2/2017 |
| CN | 107922866 A | 4/2018 |
| EP | 1 556 420 A1 | 7/2005 |

(Continued)

OTHER PUBLICATIONS

Combined Taiwanese Office Action and Search Report issued Apr. 2, 2024, in corresponding Taiwanese Patent Application No. 109124967 (with English Translation), 16 pages.
Office Action issued Aug. 24, 2023, in corresponding Indonesian Patent Application No. P00202201330 (with English Translation), 4 pages.
Office Action issued Jan. 9, 2024, in corresponding Japanese Patent Application No. 2021-534030 (with English Translation), 6 pages.
Written Opinion issued Feb. 21, 2023, in corresponding Singapore Patent Application No. 11202200588X, 7 pages.

(Continued)

*Primary Examiner* — In Suk C Bullock
*Assistant Examiner* — Jason Y Chong
(74) *Attorney, Agent, or Firm* — Oblon, McClelland, Maier & Neustadt, L.L.P.

(57) ABSTRACT

A saturated aliphatic hydrocarbon compound composition having an evaporation loss of 4% by mass or less as determined by the Noack method, a kinetic viscosity at 100° C. of 6.5 mm2/s or less, and an average carbon number of 36 to 44. A lubricating oil composition may contain such a saturated aliphatic hydrocarbon compound composition. A method for producing a saturated aliphatic hydrocarbon compound composition, may include: (1) oligomerizing an olefin to obtain an olefin oligomer; (2) isomerizing the olefin oligomer to obtain an isomer; and (3) hydrogenating the isomer.

19 Claims, No Drawings

(56) References Cited

U.S. PATENT DOCUMENTS

| | | | |
|---|---|---|---|
| 2017/0183594 A1 | 6/2017 | Courtiade et al. | |
| 2018/0187117 A1 | 7/2018 | Courtiade et al. | |

FOREIGN PATENT DOCUMENTS

| | | |
|---|---|---|
| EP | 1 880 986 A1 | 1/2008 |
| EP | 1 966 351 A1 | 9/2008 |
| EP | 2 275 516 A1 | 1/2011 |
| EP | 3 313 963 A1 | 5/2018 |
| GB | 961903 | 6/1964 |
| JP | 2004-532328 A | 10/2004 |
| JP | 2006-503973 A | 2/2006 |
| JP | 2006-342149 A | 12/2006 |
| JP | 2008-132104 A | 6/2008 |
| JP | 2008-143958 A | 6/2008 |
| JP | 2009-517523 A | 4/2009 |
| JP | 2009-218117 A | 9/2009 |
| JP | 2018-519393 A | 7/2018 |
| JP | 2018-132104 A | 8/2018 |
| JP | 7525491 B2 | 7/2024 |
| KR | 2003-0097860 A | 12/2003 |
| TW | 201035010 A1 | 10/2010 |
| WO | WO 02/092729 A1 | 11/2002 |
| WO | WO 2004/039850 A1 | 5/2004 |
| WO | WO 2006/120925 A1 | 11/2006 |
| WO | WO 2007/064392 A1 | 6/2007 |
| WO | WO 2012/134688 A1 | 10/2012 |
| WO | WO 2017/001442 A1 | 1/2017 |
| WO | WO 2019/014540 A1 | 1/2019 |

OTHER PUBLICATIONS

Saudi Arabian Office Action issued Oct. 26, 2023 in Saudi Arabian Application No. 522431437, (with English translation), 10 pages.
Indian Office Action issued Jun. 26, 2023 in Indian Application No. 202247003462, 6 pages.
Extended European Search Report issued Jul. 4, 2023 in European Application No. 20844170.9, 7 pages.
Combined Chinese Office Action and Search Report issued Oct. 27, 2022 in Chinese Application No. 202080052938.1, 11 pages.
International Search Report mailed on Oct. 6, 2020 in PCT/JP2020/028118 filed on Jul. 20, 2020 (3 pages).
Office Action issued Jul. 2, 2024, in corresponding Indian Patent Application No. 202247003462 (with English Translation), 4 pages.
Vietnamese Office Action issued Aug. 20, 2024, in Vietnamese Patent Application No. 1-2022-00934, (with English translation), 4 pages.
Office Action issued on Dec. 15, 2024 in Korean Application No. 10-2022-7005498 (with English Translation) 9 pages.
Official communication issued on Apr. 7, 2025, in corresponding Canadian Application No. 3,148,235.

* cited by examiner

SATURATED ALIPHATIC HYDROCARBON COMPOUND COMPOSITION, LUBRICANT COMPOSITION, AND METHOD FOR PRODUCING SATURATED ALIPHATIC HYDROCARBON COMPOUND COMPOSITION

CROSS-REFERENCE TO RELATED APPLICATIONS

The present application is the national stage of international application PCT/JP2020/028118, filed on Jul. 20, 2020, and claims the benefit of the filing date of Japanese Appl. No. 2019-137092, filed on Jul. 25, 2019.

TECHNICAL FIELD

The present invention relates to a saturated aliphatic hydrocarbon compound composition, a lubricating oil composition, and a method for producing a saturated aliphatic hydrocarbon compound composition.

BACKGROUND ART

In recent years, lubricating oils are required to have high durability from the viewpoint of resource saving as well as environmental protection. In order for a lubricating oil to have high durability, the lubricating oil needs to be stable to heat and oxidation reaction.

Various synthetic lubricating oils have been developed as such lubricating oils having excellent stability. Such synthetic lubricating oils use, as a base oil, a poly(α-olefin), a polybutene, an alkylbenzene, a polyol ester, a dibasic acid ester, a polyoxyalkylene glycol, a polyoxyalkylene glycol ester, a polyoxyalkylene glycol ether, a silicone, etc.

Among them, a poly(α-olefin), which has high chemical stability and an excellent viscosity index, is widely used. A poly(α-olefin) having an intended viscosity is produced by adjusting an α-olefin as a starting material and the polymerization degree, and is practically used. Further, attempts have been made to efficiently obtain a poly(α-olefin) having a controlled structure.

For example, patent document 1 discloses a method which involves dimerizing an α-olefin in the presence of a Ziegler catalyst, and further dimerizing the resulting dimer in the presence of a Friedel-Crafts catalyst or an acid catalyst, followed by hydrogenation of the resulting product to obtain a particular saturated aliphatic hydrocarbon such as 11,13-dioctyl-13-methyltricosane. Patent document 2 discloses a method for obtaining a component of a lubricating oil composition, which is excellent in oxidation stability, heat stability and low-temperature stability. The method comprises dimerizing an α-olefin in the presence of a metallocene complex catalyst to produce a vinylidene olefin, and further dimerizing the vinylidene olefin in the presence of an acid catalyst, and then hydrogenating the resulting dimer to produce a saturated aliphatic hydrocarbon compound.

Patent document 3 discloses a method for obtaining a low-viscosity oil comprising 9-methyl-11,13-dioctyltricosane. The method involves oligomerizing 1-decene in the presence of hydrogen, a metallocene catalyst and an activator compound, catalytically hydrogenating the oligomerized product in the presence of hydrogen and a hydrogenation catalyst, and isolating the resulting tetramer fraction by distillation under reduced pressure.

CITATION LIST

Patent Literature

Patent document 1: British Patent No. GB %1,903
Patent document 2: Japanese Patent Laid-Open Publication No. JP2006-342149
Patent document 3: Published Japanese Translation No. JP2018-519393 of the PCT International Publication

SUMMARY OF INVENTION

Technical Problem

A low-viscosity base oil is generally required for lubricating oils for machines. A poly(α-olefin) having a low viscosity is obtained e.g. by adjusting the polymerization degree, as described above. A low-viscosity poly(α-olefin) necessarily has a low molecular weight. Such a low-molecular weight poly(α-olefin) evaporates easily and thus has the problem of poor durability.

A demand therefore exists for a poly(α-olefin) which serves as a base oil of a lubricating oil, and which has a low viscosity and yet has excellent evaporation resistance so as to achieve both good lubricating properties and good durability.

It is, therefore, an object of the present invention to provide a saturated aliphatic hydrocarbon compound composition which has a low viscosity and a low evaporation loss and which, when used as a base oil, can provide a long-life lubricating oil, to provide a lubricating oil composition containing the saturated aliphatic hydrocarbon compound composition, and to provide a method for producing a saturated aliphatic hydrocarbon compound composition.

Solution to Problem

The present inventors, through intensive studies to solve the above problem, have found that a saturated aliphatic hydrocarbon compound composition, having particular physical properties and a particular average carbon number, has a low viscosity and a low evaporation loss and, when used as a base oil, can provide a long-life lubricating oil. This finding has led to the present invention. The present inventors have also found that a method, which involves isomerizing an olefin oligomer and hydrogenating the isomerized product, can produce a saturated aliphatic hydrocarbon compound composition which is useful as a base oil of a lubricating oil.

Thus, the present invention relates to the following (1) to (13).

(1) A saturated aliphatic hydrocarbon compound composition having an evaporation loss of 4% by mass or less as determined by the Noack method, a kinematic viscosity at 100° C. of 6.5 mm$^2$/s or less, and an average carbon number of 36 to 44.

(2) The saturated aliphatic hydrocarbon compound composition as described in (1), wherein the content of a saturated aliphatic hydrocarbon compound having a carbon number of 40 is 90% by mass or more.

(3) The saturated aliphatic hydrocarbon compound composition as described in (1) or (2), wherein in a gas chromatography chromatogram of the composition, the area of the main peak is 40% or less of the total peak area corresponding to a saturated aliphatic hydrocarbon compound having a carbon number of 40.

(4) The saturated aliphatic hydrocarbon compound composition as described in any one of (1) to (3), wherein the content of 11-methyl-11,13-dioctyltricosane in a saturated aliphatic hydrocarbon compound having a carbon number of 40 is 40% by mass or less.

(5) A lubricating oil composition containing the saturated aliphatic hydrocarbon compound composition as described in any one of (1) to (4).

(6) A method for producing a saturated aliphatic hydrocarbon compound composition, comprising: a step 1 of oligomerizing an olefin to obtain an olefin oligomer; a step 2 of isomerizing the olefin oligomer to obtain an isomer; and a step 3 of hydrogenating the isomer.

(7) The method for producing a saturated aliphatic hydrocarbon compound composition as described in (6), wherein in the step 2, the olefin oligomer is isomerized in the presence of a Friedel-Crafts catalyst.

(8) The method for producing a saturated aliphatic hydrocarbon compound composition as described in (6) or (7), wherein in the step 1, the olefin is oligomerized in the presence of a Friedel-Crafts catalyst.

(9) The method for producing a saturated aliphatic hydrocarbon compound composition as described in (7) or (8), wherein the Friedel-Crafts catalyst comprises an organoaluminum compound.

(10) The method for producing a saturated aliphatic hydrocarbon compound composition as described in any one of (6) to (9), further comprising a step 4, which is a distillation step, after the step 3.

(11) The method for producing a saturated aliphatic hydrocarbon compound composition as described in any one of (6) to (10), wherein the olefin comprises 90% by mass or more of an olefin having a carbon number of 20.

(12) The method for producing a saturated aliphatic hydrocarbon compound composition as described in (11), wherein the olefin is a dimer of 1-decene.

(13) A lubricating oil composition containing a saturated aliphatic hydrocarbon compound composition obtained by the production method as described in any one of (6) to (12).

Advantageous Effects of Invention

The present invention makes it possible to provide a saturated aliphatic hydrocarbon compound composition which has a low viscosity and a low evaporation loss and, when used as a base oil, can provide a long-life lubricating oil, to provide a lubricating oil composition containing the saturated aliphatic hydrocarbon compound composition, and to provide a method for producing a saturated aliphatic hydrocarbon compound composition.

DESCRIPTION OF EMBODIMENTS

The present invention provides a saturated aliphatic hydrocarbon compound composition having an evaporation loss of 4% by mass or less as determined by the Noack method, a kinematic viscosity at 100° C. of 6.5 mm$^2$/s or less, and an average carbon number of 36 to 44, provides a lubricating oil composition containing the saturated aliphatic hydrocarbon compound composition, and provides a method for producing a saturated aliphatic hydrocarbon compound composition, comprising: a step 1 of oligomerizing an olefin to obtain an olefin oligomer; a step 2 of isomerizing the olefin oligomer to obtain an isomer; and a step 3 of hydrogenating the isomer.

The present invention will now be described in detail.

[Saturated Aliphatic Hydrocarbon Compound Composition]

The saturated aliphatic hydrocarbon compound composition of the present invention has an evaporation loss of 4% by mass or less as determined by the Noack method, a kinematic viscosity at 100° C. of 6.5 mm$^2$/s or less, and an average carbon number of 36 to 44.

The average carbon number of the saturated aliphatic hydrocarbon compound composition of the present invention is 36 to 44, preferably 38 to 42, more preferably 39 to 42, and even more preferably 39 to 41.

The saturated aliphatic hydrocarbon compound composition of the present invention preferably comprises, as a component, a saturated aliphatic hydrocarbon compound having a carbon number of 40 preferably in the largest amount among all the components, more preferably as a main component.

The content of the saturated aliphatic hydrocarbon compound having a carbon number of 40 is preferably 20% by mass or more, more preferably 30% by mass or more, even more preferably 50% by mass or more, still more preferably 90% by mass or more, yet more preferably 92% by mass or more, and yet more preferably 94% by mass or more.

When the average carbon number of the composition and the content of the saturated aliphatic hydrocarbon compound having a carbon number of 40 are within the above ranges, the saturated aliphatic hydrocarbon compound composition, when used as a base oil, can provide a low-viscosity, long-life lubricating oil.

In a gas chromatography chromatogram of the saturated aliphatic hydrocarbon compound composition of the present invention, the area of the main peak is preferably 40% or less, more preferably 35% or less, even more preferably 30% or less, still more preferably 25% or less, and yet more preferably 23% or less of the total peak area corresponding to the saturated aliphatic hydrocarbon compound having a carbon number of 40.

A peak area in a gas chromatography chromatogram can be determined by the method described in Examples below, using an FID (hydrogen flame ionization detector).

As described above, the saturated aliphatic hydrocarbon compound composition of the present invention may comprise, as a main component, a saturated aliphatic hydrocarbon compound having a carbon number of 40. The saturated aliphatic hydrocarbon compound having a carbon number of 40 comprises a plurality of isomers.

Therefore, in a gas chromatography analysis of the saturated aliphatic hydrocarbon compound composition, a plurality of peaks, corresponding to the saturated aliphatic hydrocarbon compound having a carbon number of 40, appear in the chromatogram. The "main peak" refers to a peak having the largest area among the plurality of peaks.

It is not known exactly which compound corresponds to the main peak; however, it is considered to be 11-methyl-11,13-dioctyltricosane. Therefore, the content of 11-methyl-11,13-dioctyltricosane in the saturated aliphatic hydrocarbon compound having a carbon number of 40 of the saturated aliphatic hydrocarbon compound composition of the present invention is preferably 40% by mass or less, more preferably 35% by mass or less, even more preferably 30% by mass or less, still more preferably 25% by mass or less, and yet more preferably 23% by mass or less.

Though it is not known exactly why the saturated aliphatic hydrocarbon compound composition of the present invention has a low viscosity and a low evaporation loss and, when used as a base oil, can provide a long-life lubricating oil, it may be for the following reason: 11-methyl-11,13- dioctyltricosane, because of its quaternary carbon, is considered to be susceptible to oxidative decomposition due to an external stimulus such as heat. In the saturated aliphatic hydrocarbon compound composition of the present invention, the content of the saturated aliphatic hydrocarbon compound having a quaternary carbon is low; isomers having a more stable structure are contained in a larger amount in total.

Therefore, the proportion of quaternary carbon atoms per molecule is preferably 1.0% or less, more preferably 0.88% or less, even more preferably 0.75% or less, still more preferably 0.63% or less, and yet more preferably 0.58% or less of the carbon atoms in the saturated aliphatic hydrocarbon compound composition of the present invention, having an average carbon number of 36 to 44.

<Properties of Saturated Aliphatic Hydrocarbon Compound Composition>

The saturated aliphatic hydrocarbon compound composition of the present invention has the excellent properties of low viscosity and low evaporation loss.

The saturated aliphatic hydrocarbon compound composition of the present invention has an evaporation loss of 4% by mass or less, preferably 3.9% by mass or less, more preferably 3.8% by mass or less, and even preferably 3.6% by mass or less as determined by the Noack method. The evaporation loss as determined by the Noack method is preferably as low as possible and is desirably 0% by mass. However, a saturated aliphatic hydrocarbon compound composition having an average carbon number of 36 to 44 generally has an evaporation loss of 3.0% by mass or more.

The saturated aliphatic hydrocarbon compound composition of the present invention has a kinematic viscosity at 100° C. of 6.5 mm$^2$/s or less, preferably 6.3 mm$^2$/s or less, more preferably 6.1 mm$^2$/s or less, and even more preferably 6.0 mm$^2$/s or less. Though a preferable kinematic viscosity at 100° C. varies depending on the intended use of the lubricating oil, it is generally 5.0 mm$^2$/s or more in the case of a saturated aliphatic hydrocarbon compound composition having an average carbon number of 36 to 44.

The following are other properties of the saturated aliphatic hydrocarbon compound composition of the present invention.

The saturated aliphatic hydrocarbon compound composition of the present invention preferably has a kinematic viscosity at 40° C. of 40 mm$^2$/s or less, more preferably 35 mm$^2$/s or less, even more preferably 32 mm$^2$/s or less, and still more preferably 31 mm$^2$/s or less. Though a preferable kinematic viscosity at 40° C. varies depending on the intended use of the lubricating oil, it is generally 25 mm$^2$/s or more in the case of a saturated aliphatic hydrocarbon compound composition having an average carbon number of 36 to 44.

The saturated aliphatic hydrocarbon compound composition of the present invention preferably has a viscosity index of 110 or more, more preferably 120 or more, even more preferably 130 or more, and still more preferably 140 or more. Though a preferable viscosity index varies depending on the intended use of the lubricating oil, it is generally 150 or less in the case of a saturated aliphatic hydrocarbon compound composition having an average carbon number of 36 to 44.

The saturated aliphatic hydrocarbon compound composition of the present invention preferably has a cold cranking viscosity (CCS) of 4000 mPa·s or less, more preferably 3700 mPa·s or less, even more preferably 3500 mPa·s or less, and still more preferably 3400 mPa·s or less. Though a preferable cold cranking viscosity (CCS) varies depending on the intended use of the lubricating oil, it is generally 3000 mPa·s or more in the case of a saturated aliphatic hydrocarbon compound composition having an average carbon number of 36 to 44.

The saturated aliphatic hydrocarbon compound composition of the present invention preferably has a pour point of −40° C. or less, more preferably −50° C. or less.

[Method for Producing Saturated Aliphatic Hydrocarbon Compound Composition]

The method for producing a saturated aliphatic hydrocarbon compound composition of the present invention comprises: a step 1 of oligomerizing an olefin to obtain an olefin oligomer; a step 2 of isomerizing the olefin oligomer to obtain an isomer; and a step 3 of hydrogenating the isomer.

The saturated aliphatic hydrocarbon compound composition, obtained by the present production method, is preferably the above-described saturated aliphatic hydrocarbon compound composition, i.e., one having an evaporation loss of 4% by mass or less as determined by the Noack method, a kinematic viscosity at 100° C. of 6.5 mm$^2$/s or less, and an average carbon number of 36 to 44. However, depending on the intended use of the lubricating oil composition, the saturated aliphatic hydrocarbon compound composition obtained by the present production method may be one which does not meet the requirements of the above-described one. The present production method can also efficiently produce such a saturated aliphatic hydrocarbon compound composition.

The saturated aliphatic hydrocarbon compound composition, obtained by the present production method, has the excellent property of extremely low evaporation loss as determined by the Noack method, as compared to a saturated aliphatic hydrocarbon compound composition obtained by any other production method and having the same kinematic viscosity. Furthermore, compared to a saturated aliphatic hydrocarbon compound composition obtained by any other production method and having the same average carbon number, the saturated aliphatic hydrocarbon compound composition, obtained by the present production method, has the excellent property of low evaporation loss as determined by the Noack method, and low kinematic viscosity at 100° C.

The present production method will now be described in detail.

<Olefin>

A vinylidene olefin, an α-olefin, or a mixture thereof is preferred as an olefin for use in the method for producing a saturated aliphatic hydrocarbon compound composition of the present invention. A vinylidene olefin or a mixture of a vinylidene olefin and an α-olefin is more preferred, and a vinylidene olefin is even more preferred.

When the saturated aliphatic hydrocarbon compound composition having an average carbon number of 36 to 44 is obtained by the method for producing a saturated aliphatic hydrocarbon compound composition of the present invention, the content of an olefin having a carbon number of 20 in the olefin used in the present production method is preferably 80% by mass or more, more preferably 85% by mass or more, even more preferably 90% by mass or more, and still more preferably 91% by mass or more.

When the content of an olefin having a carbon number of 20 is within the above range, the saturated aliphatic hydrocarbon compound composition having an average carbon number of 36 to 44 can be obtained efficiently.

(Vinylidene Olefin)

Preferably, the vinylidene olefin is at least one selected from compounds represented by the following general formula (1):

(1)

where $R^1$ and $R^2$ each independently represent a hydrogen atom or a linear or branched alkyl group having 1 to 16 carbon atoms.

In the general formula (1), $R^1$ and $R^2$ are each independently a hydrogen atom or a linear or branched alkyl group having 1 to 16 carbon atoms, and are preferably a linear alkyl group having 8 to 16 carbon atoms in the present invention. The linear alkyl group having 8 to 16 carbon atoms includes a n-octyl group, a n-nonyl group, a n-decyl group, a n-undecyl group, a n-dodecyl group, a n-tridecyl group, a n-tetradecyl group, a n-pentadecyl group, and a n-hexadecyl group.

(Production of Vinylidene Olefin)

The vinylidene olefin is preferably produced by dimerizing an α-olefin.

The α-olefins described below under the heading "(α-olefin)" can be preferably used as an α-olefin for use in the dimerization. Among them, α-olefins having 6 to 12 carbon atoms are preferred, and α-olefins having 8 to 10 carbon atoms are more preferred. Further, linear α-olefins are preferred, linear α-olefins having 6 to 12 carbon atoms are more preferred, and linear α-olefins having 8 to 10 carbon atoms are even more preferred.

Specific examples of the α-olefin include 1-octene, 1-decene, 1-dodecene, 1-tridecene, 1-tetradecene, 1-pentadecene, 1-hexadecene, 1-heptadecene, and 1-octadecene, 1-octene, 1-decene, 1-dodecene, and 1-tetradecene are preferred, 1-octene and 1-decene are more preferred, and 1-decene is even more preferred. These α-olefins may be used singly or in a combination of two or more.

Thus, when the olefin for use in the present production method is a vinylidene olefin, it is preferably a 1-octene dimer, a 1-decene dimer, a 1-dodecene dimer, or a 1-tetradecene dimer, more preferably a 1-octene dimer or a 1-decene dimer, and even more preferably a 1-decene dimer.

The vinylidene olefin can be obtained selectively at a high yield by performing a dimerization reaction in the presence of a catalyst.

A metallocene catalyst is preferred as a catalyst for use in the dimerization of an α-olefin.

A metallocene complex catalyst comprising (i) a metallocene complex which has a ligand including a conjugated five-membered carbon ring, and contains a transition metal belonging to Groups 4 to 6 of the Periodic Table, and (ii) at least one selected from (ii-1) a compound composed of a cation and an anion in which a plurality of groups are bound to an element and (ii-2) an organoaluminum compound can be preferably used as the metallocene complex catalyst.

The component (i) constituting the catalyst, i.e., the metallocene complex which has a ligand including a conjugated five-membered carbon ring, and contains a transition metal selected from Groups 4-6 of the Periodic Table, from the viewpoint of catalytic activity, is preferably a transition metal compound represented by the following general formula (2) or (3):

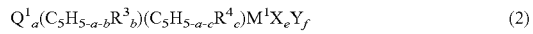

In the formulae, $Q^1$ represents a linking group that crosslinks the two conjugated five-membered ring ligands, $(C_5H_{5-a-b}R^3{}_b)$ and $(C_5H_{5-a-c}R^4{}_c)$, and $Q^2$ represents a linking group that crosslinks the conjugated five-membered ring ligand $(C_5H_{5-a-d}R^5{}_d)$ and the Z group. (e+f) is equal to (the valence of $M^1$–2). $M^1$ represents a transition metal belonging to Groups 4 to 6 of the Periodic Table. X, Y and Z each represent a covalent or ionic ligand.

Specific examples of $Q^1$ and $Q^2$ include (1) an alkylene group having 1 to 4 carbon atoms or a cycloalkylene group, which may have a lower-alkyl or phenyl side-chain substituent, such as a methylene group, an ethylene group, an isopropylene group, a methylphenyl methylene group, a diphenyl methylene group, or a cyclohexylene group, (2) a silylene group or an oligosilylene group, which may have a lower-alkyl or phenyl side-chain substituent, such as a silylene group, a dimethyl silylene group, a methylphenyl silylene group, a diphenyl silylene group, a disilylene group, or a tetramethyl disilylene group, and (3) a hydrocarbon group [a lower alkyl group, a phenyl group, a hydrocarbyloxy group (preferably a lower alkoxy group), etc.] containing germanium, phosphorus, nitrogen, boron, or aluminum, such as a $(CH_3)_2Ge$ group, a $(C_6H_3)_2$ Ge group, a $(CH_3)$ P group, a $(C_6H_5)$ P group, a $(C_4H_9)$ N group, a $(C_6H_5)$ N group, a $(CH_3)$ B group, a $(C_4H_9)$ B group, a $(C_6H_5)$ B group, a $(C_6H_5)$ Al group, or a $(CH_3O)$ Al group. Among them, an alkylene group and a silylene group are preferred from the viewpoint of catalytic activity.

$(C_5H_{5-a-b}R^3{}_b)$, $(C_5H_{5-a-c}R^4{}_c)$ and $(C_5H_{5-a-d}R^5{}_d)$ are conjugated five-membered ring ligands, in which $R^3$, $R^4$ and $R^5$ each represent a hydrocarbon group, a halogen atom, an alkoxy group, a silicon-containing hydrocarbon group, a phosphorus-containing hydrocarbon group, a nitrogen-containing hydrocarbon group, or a boron-containing hydrocarbon group. a is 0, 1 or 2. b, c and d each represent an integer of 0 to 5 when a=0, an integer of 0 to 4 when a=1, and an integer of 0 to 3 when a=2. The hydrocarbon group preferably has 1 to 20 carbon atoms, particularly preferably 1 to 12 carbon atoms. The hydrocarbon group may be a monovalent group and may bind to a cyclopentadienyl group which is a conjugated five-membered ring group. Alternatively, when a plurality of hydrocarbon groups are present, two of them may be bound to each other to form a ring structure together with part of a cyclopentadienyl group.

Thus, the conjugated five-membered ring ligands are typified by a cyclopentadienyl group, an indenyl group or a fluorenyl group, which may or may not be substituted. Examples of the halogen atom include a chlorine atom, a bromine atom, an iodine atom, and a fluorine atom. The alkoxy group is preferably one having 1 to 12 carbon atoms. The silicon-containing hydrocarbon group may be, for example, —Si($R^6$)($R^7$)($R^8$)($R^6$, $R^7$ and $R^8$ are each a hydrocarbon group having 1 to 24 carbon atoms). The phosphorus-containing hydrocarbon group, the nitrogen-containing hydrocarbon group, and the boron-containing hydrocarbon group may be, for example, —P($R^9$)($R^{10}$), —N($R^9$)($R^{10}$), and —B($R^9$)($R^{10}$) ($R^9$ and $R^{10}$ are each a hydrocarbon group having 1 to 18 carbon atoms), respectively.

When there are a plurality of $R^3$s, a plurality of $R^4$s, and a plurality of $R^5$s, the $R^3$s, $R^4$s and $R^5$s may each be the same or different from each other. Further, in the general formula (2), the conjugated five-membered ring ligands $(C_5H_{5-a-b}R^3{}_b)$ and $(C_5H_{5-a-c}R^4{}_c)$ may be the same or different from each other.

The hydrocarbon group having 1 to 24 carbon atoms or the hydrocarbon groups having 1 to 18 carbon atoms include an alkyl group, an alkenyl group, an aryl group, and an alicyclic aliphatic hydrocarbon group. The alkyl group includes a methyl group, an ethyl group, a n-propyl group, an isopropyl group, a n-butyl group, an isobutyl group, a tert-butyl group, a n-hexyl group, and a n-decyl group. The alkyl group preferably has 1 to 20 carbon atoms. The alkenyl group includes a vinyl group, a 1-propenyl group, a 1-butenyl group, a 1-hexenyl group, a 1-octenyl group, and a cyclohexenyl group. In the present invention, the alkenyl group preferably has 2 to 10 carbon atoms. The aryl group includes a phenyl group, a tolyl group, a xylyl group, and a naphthyl group. In the present invention, the aryl group preferably has 6 to 14 carbon atoms. The alicyclic aliphatic hydrocarbon group includes a cyclopropyl group, a cyclopentyl group, and a cyclohexyl group.

$M^1$ represents a transition metal belonging to Groups 4 to 6 of the Periodic Table. Specific examples of the transition metal include titanium, zirconium, hafnium, vanadium, niobium, molybdenum, and tungsten. Among them, titanium, zirconium, and hafnium are preferred from the viewpoint of catalytic activity. Z is a covalent ligand, and examples include a halogen atom, oxygen (—O—), sulfur (—S—), an alkoxy group having 1 to 20 (preferably 1 to 10) carbon atoms, a thioalkoxy group having 1 to 20 (preferably 1 to 12) carbon atoms, a nitrogen-containing hydrocarbon group (e.g., a t-butylamino group or a t-butylimino group) having 1 to 40 (preferably 1 to 18) carbon atoms, and a phosphorus-containing hydrocarbon groups having 1 to 40 (preferably 1 to 18) carbon atoms. X and Y are each a covalent or ionic ligand, and examples include a hydrogen atom, a halogen atom, a hydrocarbon group having 1 to 20 (preferably 1 to 10) carbon atoms, an alkoxy group having 1 to 20 (preferably 1 to 10) carbon atoms, an amino group, a phosphorus-containing hydrocarbon group (e.g., a diphenylphosphine group) having 1 to 20 (preferably 1 to 12) carbon atoms, a silicon-containing hydrocarbon group (e.g., a trimethylsilyl group) having 1 to 20 (preferably 1 to 12) carbon atoms, and a boron compound containing a hydrocarbon group having 1 to 20 (preferably 1 to 12) carbon atoms or a halogen-containing boron compound (e.g., $B(C_6H_5)_4$ or $BF_4$). Among them, a halogen atom and a hydrocarbon group are preferred. The X and the Y may be the same or different from each other. Among the transition metal compounds represented by the general formula (2) or (3), a complex having a ligand with an indenyl, cyclopentadienyl or fluorenyl structure is particularly preferred.

Examples of the transition metal compound represented by the general formula (2) or (3) include (a) a transition metal compound having no crosslinking group and having two conjugated five-membered ring ligands, (b) a transition metal compound having two conjugated five-membered ring ligands crosslinked by an alkylene group, (c) a transition metal compound having two conjugated five-membered ring ligands crosslinked by a silylene group, (d) a transition metal compound having two conjugated five-membered ring ligands crosslinked by a hydrocarbon group containing germanium, aluminum, boron, phosphorus, or nitrogen, (e) a transition metal compound having one conjugated five-membered ring ligand, (f) a transition metal compound having two conjugated five-membered ring ligands which are double-crosslinked, and (g) a transition metal compound corresponding to any one of the above-described compounds (a) to (f) in which a chlorine atom(s) is replaced with a bromine atom, an iodine atom, a hydrogen atom, a methyl group, a phenyl group, a benzyl group, a methoxy group, a dimethylamino group, or the like.

Among the compounds (a) to (g), the compound (c), namely the transition metal compound having two conjugated five-membered ring ligands crosslinked by a silylene group, in which the transition metal is zirconium or titanium, is preferred.

There is no particular limitation on the compound (ii-1), namely the compound composed of a cation and an anion in which a plurality of groups are bound to an element, of the component (ii) constituting the catalyst; however, compounds represented by the following formula (4) or (5) can be preferably used:

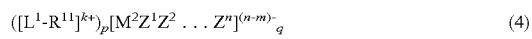

$$([L^1\text{-}R^{11}]^{k+})_p[M^2Z^1Z^2 \ldots Z^n]^{(n-m)-}_q \qquad (4)$$

$$([L^2]^{k+})_p[M^3Z^1Z^2 \ldots Z^n]^{(n-m)-}_q \qquad (5)$$

where $L^2$ is $M^4$, $R^{12}R^{13}M^5$, $R^{14}_3C$, $R^{15}R^{16}R^{17}R^{18}N$ or $R^{19}R^{20}R^{21}S$. $L^1$ represents a Lewis base, and $R^{11}$ represents a hydrogen atom, an alkyl group having 1 to 20 carbon atoms, an aryl group having 6 to 20 carbon atoms, an alkylaryl group or an arylalkyl group. $M^2$ and $M^3$ are each an element selected from Group 13, Group 14, Group 15, Group 16 and Group 17 of the Periodic Table. $Z^1$ to $Z^n$ each represent a hydrogen atom, a dialkylamino group, an alkoxy group having 1 to 20 carbon atoms, an aryloxy group having 6 to 20 carbon atoms, an alkyl group having 1 to 20 carbon atoms, an aryl group having 6 to 20 carbon atoms, an alkylaryl group, an arylalkyl group, a halogen-substituted hydrocarbon group having 1 to 20 carbon atoms, an acyloxy group having 1 to 20 carbon atoms, an organometalloid group or a halogen atom. Two or more of $Z^1$ to $Z^n$ may bind together to form a ring.

m represents the valence of each of $M^2$ and $M^3$ and is an integer of 1 to 7, n is an integer of 2 to 8, k represents the ion valence of each of $[L^1\text{-}R^{11}]$ and $[L^2]$ and is an integer of 1 to 7, p is an integer equal to or greater than 1, and $q=(p \times k)/(n-m)$.

$M^4$ represents an element selected from Groups 1 and 11 of the Periodic Table, $M^5$ represents an element selected from Group 8, Group 9 and Group 10 of the Periodic Table, $R^{12}$ and $R^{13}$ each represent a cyclopentadienyl group, a substituted cyclopentadienyl group, an indenyl group or a fluorenyl group, $R^{14}$ represents an alkyl group having 1 to 20 carbon atoms, an aryl group, an alkylaryl group or an arylalkyl group. $R^{15}$ to $R^{21}$ each represent a hydrogen atom, a halogen atom, an alkyl group having 1 to 20 carbon atoms, an aryl group having 6 to 20 carbon atoms, an alkylaryl group, an arylalkyl group, a substituted alkyl group or an organometalloid group.

Specific examples of the Lewis base (L') include: ammonia; amines such as methylamine, aniline, dimethylamine, diethylamine, N-methylaniline, diphenylamine, trimethylamine, triethylamine, tri-n-butylamine, N,N-dimethylaniline, methyldiphenylamine, pyridine, p-bromo-N,N-dimethylaniline, and p-nitro-N,N-dimethylaniline; phosphines such as triethyl phosphine, triphenyl phosphine, and diphenyl phosphine; ethers such as dimethyl ether, diethyl ether, tetrahydrofuran, and dioxane; thioethers such as diethyl thioether and tetrahydrothiophene; and ester such as ethyl benzoate.

$M^2$ and $M^3$ are each exemplified by B and Al. $M^4$ is exemplified by Na, Ag and Cu. $M^3$ is exemplified by Fe and Co.

Among the compounds represented by the general formula (4) or (5), compounds in which $M^2$ or $M^3$ is boron are preferred, and compounds represented by the general formula (4) in which $M^2$ is boron are especially preferred.

The organoaluminum compound (ii-2) of the component (ii), constituting the catalyst, includes compounds represented by the following formula (6), (7) or (8).

$$R^{22}{}_rAlQ^3{}_{3-r} \quad (6)$$

where $R^{22}$ represents a hydrocarbon group such as an alkyl group having 1 to 20 (preferably 1 to 12) carbon atoms, an alkenyl group, an aryl group, or an aryl alkyl group, $Q^3$ represents a hydrogen atom, an alkoxy group having 1 to 20 carbon atoms, or a halogen atom, and r is a numeral of 1 to 3.

A linear aluminoxane represented by the formula:

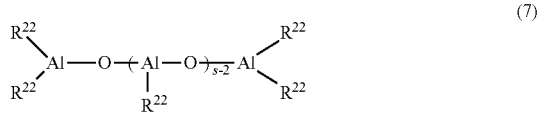

where $R^{22}$ is the same as the one described above, and s represents the degree of polymerization, which is generally 3 to 50.

A cyclic alkylaluminoxane represented by the formula:

where $R^{22}$ is the same as the one described above, and s represents the degree of polymerization, which is preferably 3 to 50.

The catalyst for use in the present invention includes a catalyst mainly comprising the component (i) and the component (ii-1), a catalyst mainly comprising the component (i) and the component (ii-2), and a catalyst mainly comprising the component (i), the component (ii-1), and the component (ii-2). When the component (ii-1) is used, no limitation is placed on conditions for use of the component (i) and the component (ii-1). However, it is preferred that the ratio (molar ratio) between the component (i) and the component (ii-1) be 1:0.01 to 1:100, particularly 1:1 to 1:10. The catalyst is preferably used at a temperature in the range of $-100°$ C. to $250°$ C., while the pressure and the processing time can be arbitrarily set. When the component (ii-2) is used, the amount of the component (ii-2) is generally 1 to 1000 mols, preferably 3 to 600 mots per mol of the component (i). The use of the component (ii-2) can enhance the catalytic activity; however, the use of the component (ii-2) in a too large amount will lead to a waste of the organoaluminum compound. The component (i) and the component (ii-1) may be brought into contact with each other in advance, followed by isolation and washing of the contact product before use. Alternatively, the component (i) and the component (ii-1) may be brought into contact with each other in a reaction system. The component (ii-2) may be brought into contact with the component (i), with the component (ii-1), or with a contact product between the component (i) and the component (ii-1). The contact may be performed in advance or in a reaction system.

The dimerization reaction of an α-olefin can be carried out in the presence of the α-olefin and the above-described catalyst, and optionally in a hydrocarbon solvent while stirring the reaction system at a temperature of $200°$ C. or less, preferably 10 to $100°$ C. for 4 to 200 hours, preferably 8 to 100 hours. The reaction pressure is usually ordinary pressure or increased pressure. After completion of the reaction, the catalyst is deactivated with a compound having a hydroxy group (e.g., methanol), and then optionally washed with an acid (e.g., an aqueous hydrochloric acid solution or sulfuric acid), followed by vacuum distillation of the product (oil) to obtain a dimer (vinylidene olefin) with high purity and high yield. The hydrocarbon solvent may be an aromatic hydrocarbon such as benzene, toluene, xylene, ethylbenzene, cumene, or cymene; an aliphatic hydrocarbon such as pentane, hexane, heptane, octane, decane, dodecane, hexadecane, or octadecane; an alicyclic hydrocarbon such as cyclopentane, cyclohexane, cyclooctane, or methylcyclopentane; or a halogenated hydrocarbon such as chloroform or dichloromethane. These solvents may be used singly or in a combination of two or more.

(α-olefin)

The α-olefin refers to an alkene having a carbon-carbon double bond in the α position (at the terminal). The below-described α-olefin can be used in the production of the above-described vinylidene olefin and also in the below-described step 1 (step of obtaining an olefin oligomer) in the method for producing a saturated aliphatic hydrocarbon compound composition.

The α-olefin for use in the production of the vinylidene olefin is preferably an α-olefin having 6 to 12 carbon atoms, more preferably an α-olefin having 8 to 10 carbon atoms.

Further, a linear α-olefin represented by the following general formula is preferred.

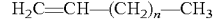

$$H_2C=CH-(CH_2)_n-CH_3$$

where n represents an integer of 7 to 15.

A linear α-olefin having 6 to 12 carbon atoms is more preferred, and a linear α-olefin having 8 to 10 carbon atoms is even more preferred.

Specific examples of the α-olefin include 1-octene, 1-decene, 1-dodecene, 1-tridecene, 1-tetradecene, 1-pentadecene, 1-hexadecene, 1-heptadecene, and 1-octadecene. Among them, 1-octene, 1-decene, 1-dodecene, and 1-tetradecene are preferred, and 1-octene and 1-decene are more preferred. These α-olefins may be used singly or in a combination of two or more.

The α-olefin for use in the below-described step 1 (step of obtaining an olefin oligomer) in the method for producing a saturated aliphatic hydrocarbon compound composition is preferably an α-olefin having 6 to 12 carbon atoms, more preferably an α-olefin having 8 to 10 carbon atoms.

Further, a linear α-olefin represented by the following general formula is preferred.

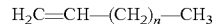

$$H_2C=CH-(CH_2)_n-CH_3$$

where n represents an integer of 7 to 15.

A linear α-olefin having 6 to 12 carbon atoms is more preferred, and a linear α-olefin having 8 to 10 carbon atoms is even more preferred.

Specific examples of the α-olefin include 1-octene, 1-decene, 1-dodecene, 1-tridecene, 1-tetradecene, 1-pentadecene, 1-hexadecene, 1-heptadecene, and 1-octadecene. Among them, 1-octene, 1-decene, 1-dodecene, and 1-tetradecene are preferred, and 1-octene and 1-decene are more preferred. These α-olefins may be used singly or in a combination of two or more.

<Step 1 (Step of Obtaining Olefin Oligomer)>

The method for producing a saturated aliphatic hydrocarbon compound composition of the present invention includes the step 1 of oligomerizing the above-described olefin to obtain an olefin oligomer.

In this step, the above-described olefin is oligomerized in the presence of a catalyst to obtain an olefin oligomer.

An acid catalyst is preferably used in this step.

The acid catalyst includes a Friedel-Crafts catalyst, a solid acid catalyst, a Lewis acid catalyst, and a Bronsted acid catalyst. Among them, a Friedel-Crafts catalyst is preferred. Thus, the oligomerization in the step 1 is preferably performed in the presence of a Friedel-Crafts catalyst.

The Friedel-Crafts catalyst preferably comprises an organoaluminum compound, and more preferably comprises an organoaluminum compound and an organic halide.

The organoaluminum compound may be a trialkylaluminum, a dialkylaluminum halide, an alkylaluminum dihalide, or the like. A dialkylaluminum halide is preferred.

Specific examples of the organoaluminum compound include trimethylaluminum, triethylaluminum, triisobutylaluminum, diethylaluminum chloride, ethylaluminum sesquichloride, and ethylaluminum dichloride. Among them, diethylaluminum chloride is preferred.

The organic halide may be an alkyl halide or an aryl halide. An alkyl halide is preferred.

Specific examples of the alkyl halide include t-butyl chloride, sec-butyl chloride, cyclohexyl chloride, and 2,5-dimethyl-2-chlorohexane. t-butyl chloride is preferred.

The molar ratio between the organoaluminum compound and the organic halide (organoaluminum compound/organic halide) in this step is preferably 1/10 to 1/0.5, more preferably 1/5 to 1/1, and even more preferably 1/4 to 1/2. When the ratio is 1/10 or more, the halogen content of the resulting oligomer can be reduced, leading to easy removal of halogen. When the ratio is 1/0.5 or less, the reaction can be performed with high reproducibility.

The concentration of the Friedel-Crafts catalyst used in this step, as determined in terms of the molar amount of aluminum per volume of the substrate (olefin) at 25° C., is preferably 0.5 to 50 mmol/L, more preferably 0.6 to 20 mmol/L, even more preferably 0.8 to 10 mmol/L, and still more preferably 1 to 5 mmol/L. When the concentration of the catalyst is 0.5 mmol/L or more, the reaction can be performed with high reproducibility. When the concentration of the catalyst is 50 mmol/L or less, the halogen content of the resulting oligomer can be reduced, leading to easy removal of halogen.

Preferably, prior to initiating the reaction in this step, a treatment is performed to remove moisture, an oxidation product, etc. from the olefin. The treatment may be performed, for example, by a method which involves putting an adsorbent in the olefin for adsorption removal of moisture, etc., or a method which involves bubbling an inert gas or a dried gas into the olefin to remove moisture, etc. with a gas flow. Such methods are preferably used in combination.

Activated alumina or a molecular sieve is preferably used as the adsorbent.

Nitrogen gas is preferably used as a bubbling gas.

As described above, a vinylidene olefin, an α-olefin, and a mixture of vinylidene olefin and an α-olefin are preferred for use in this step. A vinylidene olefin and a mixture of a vinylidene olefin and an α-olefin are more preferred, and a vinylidene olefin is even more preferred. Specific examples of preferred olefins are described above.

The dimerization reaction is allowed to proceed through contact between the catalyst and the olefin.

The reaction temperature upon the dimerization reaction is preferably 0 to 100° C., more preferably 25 to 95° C., and even more preferably 30 to 80° C. When the reaction temperature is 0° C. or more, the time until the initiation of the reaction can be reduced and, in addition, the reaction can be performed with high reproducibility. When the reaction temperature is 100° C. or less, the intended oligomer can be obtained at a high yield without deactivation of the catalyst and a side reaction such as isomerization of the olefin.

The reaction is an exothermic reaction; therefore, the reaction temperature increases during the reaction. The maximum reaction temperature is preferably adjusted to be within the above range. The end point of the reaction can be determined by detection of no generation of heat.

<Step 2 (Step of Obtaining Isomer)>

The method for producing a saturated aliphatic hydrocarbon compound composition of the present invention includes the step 2 of isomerizing the olefin oligomer, obtained in the step 1 (oligomerization step), to obtain an isomer.

This step is a step of isomerizing the olefin oligomer obtained in the step 1 (oligomerization step) to obtain an isomer in the presence of a catalyst.

The reaction mixture obtained in the step 1 (oligomerization step) may be used as it is, or after removing the catalyst from it, as a starting olefin oligomer in this step. It is preferred to use the reaction mixture as it is from the viewpoint of production efficiency.

An acid catalyst is preferably used in this step.

The acid catalyst includes a Friedel-Crafts catalyst, a solid acid catalyst, a Lewis acid catalyst, and a Bronsted acid catalyst. Among them, a Friedel-Crafts catalyst is preferred. Thus, the isomerization in the step 2 is preferably performed in the presence of a Friedel-Crafts catalyst.

The Friedel-Crafts catalyst preferably comprises an organoaluminum compound, and more preferably comprises an organoaluminum compound and an organic halide.

The organoaluminum compound may be a trialkylaluminum, a dialkylaluminum halide, an alkylaluminum dihalide, or the like. A dialkylaluminum halide is preferred.

Specific examples of the organoaluminum compound include trimethylaluminum, triethylaluminum, triisobutylaluminum, diethylaluminum chloride, ethylaluminum sesquichloride, and ethylaluminum dichloride. Among them, diethylaluminum chloride is preferred.

The organic halide may be an alkyl halide or an aryl halide. An alkyl halide is preferred.

Specific examples of the alkyl halide include t-butyl chloride, sec-butyl chloride, cyclohexyl chloride, and 2,5-dimethyl-2-chlorohexane. t-butyl chloride is preferred.

The molar ratio between the organoaluminum compound and the organic halide (organoaluminum compound/organic halide) in this step is preferably 1/10 to 1/0.5, more preferably 1/5 to 1/1, and even more preferably 1/4 to 1/2. When the ratio is 1/10 or more, the halogen content of the resulting oligomer can be reduced, leading to easy removal of halogen. When the ratio is 1/0.5 or less, the reaction can be performed with high reproducibility.

The concentration of the Friedel-Crafts catalyst used in this step, as determined in terms of the molar amount of aluminum per volume of the substrate (oligomer) at 25° C., is preferably 0.5 to 100 mmol/L, more preferably 1 to 40 mmol/L, even more preferably 1.5 to 20 mmol/L, and still more preferably 2 to 10 mmol/L. When the concentration of the catalyst is 0.5 mmol/L or more, the reaction can be performed with high reproducibility. When the concentration of the catalyst is 100 mmol/L or less, the halogen content of the resulting isomer can be reduced, leading to easy removal of halogen. In the case where a Friedel-Crafts catalyst is used in the step 1 (step of obtaining an olefin oligomer), and the reaction mixture obtained in the step 1 is used as it is in the step 2, the above-described concentration of the Friedel-Crafts catalyst refers to the concentration of the total amount of the catalyst, including the catalyst used in the step 1.

The reaction temperature upon the isomerization reaction is preferably 120 to 200° C., more preferably 130 to 190° C., and even more preferably 140 to 180° C. When the reaction temperature is 120° C. or more, the isomerization proceeds efficiently in a short time. When the reaction temperature is 200° C. or less, the intended isomer can be obtained at a high yield without a degradation reaction.

It appears that an olefin oligomer, obtained in the step 1, is isomerized into a more stable structure by performing the isomerization at a predetermined temperature using the above-described catalyst. Though the reason for this is not fully elucidated, the following is considered a main cause. When a dimer of 1-decene, for example, is used in the step 1, the resulting olefin oligomer will mainly comprise 13-methyl-11,13-dioctyltricosa-11-ene, 13-methyl-11,13-dioctyltricosa-10-ene, and 11-methyl-11-octyl-13-octylidene-tricosane. If such products, as they are, are subjected to hydrogenation, 11-methyl-11,13-dioctyltricosane, having a methyl group in the 11-position and a quaternary carbon atom bound to the methyl group, will be obtained. When the compound is used as a lubricating oil, the quaternary carbon moiety will be susceptible to decomposition, resulting in a high evaporation loss. On the other hand, the isomerization according to the production method of the present invention will reduce the quaternary carbon moiety and provide a product which is unlikely to decompose even under severe conditions, such as those of the Noack test, and thus has a low evaporation loss.

The reaction time of the isomerization reaction is preferably 1 to 240 minutes, more preferably 2 to 180 minutes, even more preferably 3 to 160 minutes, and still more preferably 5 to 140 minutes. When the reaction time is 240 minutes or less, the intended isomer can be obtained at a high yield without a side reaction such as a polymerization reaction.

The isomerization reaction is preferably terminated by adding an alkali, such as sodium hydroxide, to the reaction system.

After termination of the reaction, the reaction mixture is preferably washed with water to remove the catalyst, a salt derived from the catalyst, etc. The washing with water is preferably performed in such a manner that the reaction mixture, which has once been made alkaline, is brought to neutral, and that the pH of water used in the washing becomes 9 or less.

<Step 3 (Step of Hydrogenating Isomer)>

The method for producing a saturated aliphatic hydrocarbon compound composition of the present invention includes the step 3 of hydrogenating the isomer obtained in the step 2 (isomerization step).

In the present hydrogenation step, a saturated aliphatic hydrocarbon compound composition is preferably produced by gas-phase hydrogenation of the above-described isomer using a hydrogenation catalyst.

A common gas-phase hydrogenation method can be used in the hydrogenation step. When a noble metal catalyst, such as palladium or platinum, is used as the hydrogenation catalyst, the reaction is preferably carried out at a reaction temperature of 60 to 100° C. and a hydrogen pressure of 0.1 to 1 MPa. When a nickel catalyst is used, the reaction is preferably carried out at a reaction temperature of 150 to 250° C. and a hydrogen pressure of 1 to 20 MPa. In either catalytic system, the catalytic amount is generally 0.05 to 50% by mass of the amount of the isomer, and the hydrogenation reaction is complete in 2 to 48 hours. The hydrogenation reaction proceeds rapidly by using the above-described hydrogenation catalyst. An additional operation, e.g. to raise the temperature or pressure of the reaction system, may be carried out even after noticeable hydrogen absorption ceases in order to completely perform hydrogenation of a small amount of residual unsaturated hydrocarbon compound.

<Step 4 (Distillation Step)>

The method for producing a saturated aliphatic hydrocarbon compound composition of the present invention preferably includes a step 4, which is a distillation step, after the step 3 (hydrogenation step).

It is preferred to perform the present distillation step in order to remove impurities or a hydrocarbon compound having an unintended carbon number.

The distillation conditions may be appropriately changed e.g. depending on the carbon number of the intended saturated aliphatic hydrocarbon compound composition.

<Saturated Aliphatic Hydrocarbon Compound Composition Obtained by the Production Method>

In a gas chromatography chromatogram of the saturated aliphatic hydrocarbon compound composition obtained by the production method of the present invention, the area of the main peak is preferably 40% or less, more preferably 35% or less, even more preferably 30% or less, still more preferably 25% or less, yet more preferably 23% or less, and yet more preferably 20% or less of the total peak area corresponding to a saturated aliphatic hydrocarbon compound having a particular carbon number (main component) whose content is the highest among all the components.

A peak area in a gas chromatography chromatogram can be determined by the method described in Examples below, using an FID (hydrogen flame ionization detector).

In a gas chromatography analysis of the saturated aliphatic hydrocarbon compound composition, a plurality of peaks, corresponding to the saturated aliphatic hydrocarbon compound having a particular carbon number (main component) whose content is the highest among all the components, appear in the chromatogram. The "main peak" refers to a peak having the largest area among the plurality of peaks.

The proportion of quaternary carbon atoms per molecule is preferably 1.0% or less, more preferably 0.88% or less, even more preferably 0.75% or less, still more preferably 0.63% or less, yet more preferably 0.58% or less, and yet more preferably 0.5% or less of the carbon atoms in the saturated aliphatic hydrocarbon compound composition obtained by the production method of the present invention.

[Lubricating Oil Composition]

The lubricating oil composition of the present invention contains the above-described saturated aliphatic hydrocarbon compound composition. Thus, the lubricating oil composition of the present invention contains the saturated aliphatic hydrocarbon compound composition having an evaporation loss of 4% by mass or less as determined by the Noack method, a kinematic viscosity at 100° C. of 6.5 mm$^2$/s or less, and an average carbon number of 36 to 44.

The content of the saturated aliphatic hydrocarbon compound composition in the lubricating oil composition is preferably 55% by mass or more, more preferably 60% by mass or more. When the content is 55% by mass or more, there is little volatilization of the lubricant base oil and a loss of its weight is reduced, and therefore oil change frequency can be reduced.

The lubricating oil composition of the present invention includes a lubricating oil composition containing the saturated aliphatic hydrocarbon compound composition obtained by the above-described production method. Thus, the lubricating oil composition of the present invention contains the saturated aliphatic hydrocarbon compound composition obtained by the production method comprising the step 1 of oligomerizing an olefin to obtain an olefin oligomer, the step 2 of isomerizing the olefin oligomer to obtain an isomer, and the step 3 of hydrogenating the isomer.

The content of the saturated aliphatic hydrocarbon compound composition, obtained by the above-described production method, in the lubricating oil composition is preferably 55% by mass or more, more preferably 60% by mass or more. When the content is 55% by mass or more, there is little volatilization of the lubricant base oil and a loss of its weight is reduced, and therefore oil change frequency can be reduced.

Various additives can be used in the lubricating oil composition of the present invention as long as the effect of the present invention is not impaired.

Examples of the additives include an antioxidant, an oily agent, an extreme-pressure agent, a detergent-dispersant, a viscosity index improver, a rust inhibitor, a metal deactivator, and an antifoaming agent.

An amine antioxidant, a phenolic antioxidant and a sulfur antioxidant, which are used in conventional synthetic hydrocarbon lubricating oils, can be used as the antioxidant. These antioxidants may be used singly or in a combination of two or more.

The amount of the antioxidant is generally about 0.01 to 10% by mass, preferably 0.03 to 5% by mass based on the total amount of the lubricating oil.

The oily agent includes an aliphatic alcohol, a fatty acid compound such as a fatty acid and a fatty acid metal salt, an ester compound such as a polyol ester, a sorbitan ester and a glyceride, and an amine compound such as an aliphatic amine.

The amount of the oily agent is generally about 0.1 to 30% by mass, preferably 0.5 to 10% by mass based on the total amount of the lubricating oil from the viewpoint of the effect of the agent.

The extreme-pressure agent includes a sulfur extreme-pressure agent, a phosphorus extreme-pressure agent, an extreme-pressure agent containing sulfur and a metal, and an extreme-pressure agent containing phosphorus and a metal. These extreme-pressure agents may be used singly or in a combination of two or more. Any extreme-pressure agent may be used as long as it contains a sulfur atom and/or a phosphorus atom in the molecule and can achieve good load bearing properties and wear resistance.

The amount of the extreme-pressure agent is generally about 0.01 to 30% by mass, preferably 0.01 to 10% by mass based on the total amount of the lubricating oil composition from the viewpoint of economy and the effect of the agent.

The detergent-dispersant includes a metal sulfonate, a metal salicylate, a metal phenate, and a succinic imide. The amount of the detergent-dispersant is generally about 0.1 to 30% by mass, preferably 0.5 to 10% by mass based on the total amount of the lubricating oil composition from the viewpoint of the effect of the agent.

Examples of the viscosity index improver include polymethacrylate, dispersed polymethacrylate, an olefin copolymer (e.g., an ethylene-propylene copolymer), a dispersed olefin copolymer, and a styrene copolymer (e.g., a hydrogenated styrene-diene copolymer). The amount of the viscosity index improver is generally about 0.5 to 35% by mass, preferably 1 to 15% by mass based on the total amount of the lubricating oil composition from the viewpoint of the effect of the agent.

The rust inhibitor includes a metal sulfonate and a succinic acid ester. The amount of the rust inhibitor is generally about 0.01 to 10% by mass, preferably 0.05 to 5% by mass based on the total amount of the lubricating oil composition from the viewpoint of the effect of the agent.

The metal deactivator includes benzotriazole and thiadiazole. The amount of the metal deactivator is generally about 0.01 to 10% by mass, preferably 0.01 to 1% by mass based on the total amount of the lubricating oil composition from the viewpoint of the effect of the agent.

The antifoaming agent includes a methyl silicone oil, a fluorosilicone oil, and polyacrylate. The amount of the antifoaming agent is generally about 0.0005 to 0.01% by mass based on the total amount of the lubricating oil composition from the viewpoint of the effect of the agent.

The lubricating oil composition of the present invention can concomitantly use any other base oil as long as the intended effect of the present invention is not impaired. The other base oil can be appropriately selected from among mineral oils and synthetic oils.

EXAMPLES

The following examples illustrate the present invention in greater detail and are not intended to limit the scope of the invention.

Saturated aliphatic hydrocarbon compound compositions, obtained in Examples and Comparative Examples, were analyzed and evaluated in the following manner.

(1) Composition (Distribution of Carbon Number)

A solution of 0.1 g of a saturated aliphatic hydrocarbon compound composition in 25 mL of toluene was subjected to gas chromatography using a gas chromatograph (Agilent 6890N, manufactured by Agilent Technologies, Inc.) under the following conditions. Components corresponding to varying carbon numbers were calculated from the resulting chromatogram to determine the composition (distribution of carbon number).

(Measurement Conditions)
  Column: TC-1 (30 m×0.25 mm, film thickness 0.25 μm, manufactured by GL Sciences Inc.)
  Column oven temp.: increased from 100° C. (hold time 0 min) to 320° C. (hold time 10 min) at a rate of 10° C./min
  Injection port temp.: 300° C.
  Detector temp.: 320° C.
  Detector: FID
  Carrier gas: He
  Flow rate: 1 mL/min
  Injection amount: 1.0 μL
  Split: 1/50

(2) Proportion of Main Peak Area

The composition was determined in the same manner as in (1) except that the measurement conditions were changed as follows. Peak areas corresponding to compounds having the same carbon number were calculated from the resulting chromatogram, and the proportion of the main peak area was determined.

(Measurement Conditions)
  Column: CP-SimDist (5 m×0.53 mm, film thickness 0.17 μm, manufactured by CL Sciences Inc.)
  Column oven temp.: increased from 50° C. (0.1 min) to 430° C. (15 min) at a rate of 20° C./min Injection port temp.: oven track (column oven temp. +3° C.)
Detector temp.: 430° C.
Detector: FID
Carrier gas: He
Linear velocity: 40 cm/sec
Injection mode: on-column injection
Injection amount: 0.5 µL
(3) Kinematic Viscosities at 40° C. and at 100° C.
The kinematic viscosities at 40° C. and at 100° C. were measured according to JIS K 2283.
(4) Viscosity Index
The viscosity index was measured according to JIS K 2283.
(5) Evaporation Loss as Determined by the Noack Method
The evaporation loss as determined by the Noack method was measured by the JPI-5S-41 B method.
(6) Cold Cranking Viscosity (CCS)
The cold cranking viscosity (CCS) was measured according to JIS K 2010.
(7) Pour Point
The pour point was measured according to JIS K 2269.

Production Example 1 (Production of a Vinylidene Olefin Having a Carbon Number of 20: Production of a Dimer of 1-Decene)

4.0 L of 1-decene, 0.9 g (3 mmol) of bis(cyclopentadienyl)zirconium dichloride as a metallocene complex, and methylaluminoxane (manufactured by W. R. Grace & Co., 8 mmol in term of aluminum) were sequentially placed into a nitrogen-purged three-necked flask having an interior volume of 5 liters, and the mixture was stirred at room temperature (20° C.). The reaction liquid turned from yellow to red-brown. After 48 hours from the start of the reaction, the reaction was terminated by adding methanol to the reaction liquid, and then an aqueous hydrochloric acid solution was added to the reaction liquid to wash the organic layer. Subsequently, the organic layer was subjected to vacuum distillation to obtain 3.1 L of a fraction (dimer of 1-decene) with a boiling point of 120 to 125° C./26.6 Pa. Gas chromatographic analysis of the fraction revealed that the purity of a component having a carbon number of 20 was 98.9% by mass, and the content of a vinylidene olefin having a carbon number of 20 was 97.6% by mass. The dimer of 1-decene, obtained in this production example, will be termed C20 olefin (1) in the following Examples and Comparative Examples.

Example 1 (Production of Saturated Aliphatic Hydrocarbon Compound Composition (1))

(1) Oligomerization Step (Step 1)
Activated alumina (NKHO-24, manufactured by Sumitomo Chemicals Co., Ltd.) was placed into the C20 olefin (1) obtained in Production Example 1, and the mixture was bubbled with nitrogen to remove moisture, etc. to obtain dried C20 olefin (1). A three-necked flask equipped with a three-way cock, a thermometer and a stirring bar was purged with nitrogen, and 1,968 mL of the dried C20 olefin (1) was placed into the flask. While stirring the dried C20 olefin (1), the flask was heated in an oil bath to bring the temperature of the dried C20 olefin (1) to 30° C. 6.0 mmol of tert-butyl chloride and 2.0 mmol of diethylaluminum chloride (DEAC), as a catalyst, were added to the dried C20 olefin (1). The tert-butyl chloride and the diethylaluminum chloride (DEAC) were each added in the form of a prepared solution diluted to 0.5 mol/L with the dried C20 olefin (1). 10 minutes after the addition of the catalyst, the temperature of the reaction solution began to rise, and then the rise of temperature stopped in two minutes, indicating the termination of oligomerization.

(2) Isomerization Step (Step 2)
Next, the temperature of the reaction solution was brought to 150° C., and 6.0 mmol of tert-butyl chloride and 2.0 mmol of diethylaluminum chloride (DEAC), as a catalyst, were added to the reaction solution in the above-described manner. After carrying out reaction at 150° C. for one hour, the reaction solution was cooled to 60° C., and 160 mL of a 1.0 mol/L aqueous sodium hydroxide solution was added to the reaction solution and the solution was stirred, and then the aqueous sodium hydroxide solution was removed. Subsequently, ion-exchange water was added to the solution and the mixture was stirred, followed by removal of the ion-exchange water. This operation (washing with water) was performed repeatedly and terminated when the pH of ion-exchange water after washing reached 9 or less. Magnesium sulfate for drying was added to the solution to obtain a vinylidene olefin having a carbon number of 40. Gas chromatographic analysis of the product revealed that the proportion of the main peak area was 12% of the total peak area corresponding to the component with a carbon number of 40, and that the content of the component with a carbon number of 40 in the resulting product was 60.4% by mass.

(3) Hydrogenation Step (Step 3)
Next, the vinylidene olefin having a carbon number of 40, obtained in step 2, was transferred to an autoclave, and 5 mass % palladium-alumina was added to the vinylidene olefin, and then the autoclave was purged with nitrogen, and further purged with hydrogen. Thereafter, the temperature of the vinylidene olefin was raised, and hydrogenation reaction was carried out for 24 hours under the conditions of 80° C. and a hydrogen pressure of 0.8 MPa to obtain a saturated aliphatic hydrocarbon compound composition. Gas chromatographic analysis of the product revealed that the proportion of the main peak area was 23% of the total peak area corresponding to the component with a carbon number of 40.

(4) Distillation Step
Next, the saturated aliphatic hydrocarbon compound composition, obtained in step 3, was transferred to a distillation flask, and the degree of vacuum in the distillation flask was brought to 26.6 Pa. The temperature of an oil bath was increased from room temperature to 150° C., and a low-molecular weight fraction was distilled off at 150° C. Thereafter, the oil bath was heated to 190° C., and distillation was carried out at 26.6 Pa for 30 minutes to obtain a distillation residue. The resulting distillation residue was distilled at 235° C. and 5.3 Pa with a thin-film distillation apparatus to obtain a saturated aliphatic hydrocarbon compound composition (1). The composition and properties of the resulting composition are shown in Table 1 below. The average carbon number of the resulting saturated aliphatic hydrocarbon compounds was 40.31, and the content of the saturated aliphatic hydrocarbon compound having a carbon number of 40 was 94.6% by mass.

Comparative Example 1 (Production of Saturated Aliphatic Hydrocarbon Compound Composition (2))

A saturated aliphatic hydrocarbon compound composition (2) was produced in the same manner as in Example 1 except that in the production of the saturated aliphatic hydrocarbon compound composition (1) of Example 1, the isomerization step (step 2) (2) was not performed. Gas chromatographic analysis of the product revealed that the proportion of the main peak area was 88% of the total peak area corresponding to the component with a carbon number of 40. The composition and properties of the resulting composition are shown in Table 1 below.

Comparative Example 2 (Production of Saturated Aliphatic Hydrocarbon Compound Composition (3))

A saturated aliphatic hydrocarbon compound composition (3) was produced in the same manner as in Example 1 except that in the production of the saturated aliphatic hydrocarbon compound composition (1) of Example 1, the temperature of the reaction solution in the oligomerization step (step 1) (1) was changed from 30° C. to 100° C., and the isomerization step (step 2) (2) was not performed. Gas chromatographic analysis of the product revealed that the proportion of the main peak area was 53% of the total peak area corresponding to the component with a carbon number of 40. The composition and properties of the resulting composition are shown in Table 1 below.

TABLE 1

|  |  | Example 1 | Comp. Example 1 | Comp. Example 2 |
|---|---|---|---|---|
| Step 1 (oligomerization) | Olefin | C20 olefin (1) | C20 olefin (1) | C20 olefin (1) |
|  | Catalyst | t-BuCl/ DEAC | t-BuCl/ DEAC | t-BuCl/ DEAC |
|  | Reaction temp. (° C.) | 30 | 30 | 100 |
| Step 2 (isomerization) | Catalyst | t-BuCl/ DEAC | — | — |
|  | Reaction temp. (° C.) | 150 | — | — |
| Step 3 (hydrogenation) | Catalyst | Pd/ alumina | Pd/ alumina | Pd/ alumina |
| Number of saturated aliphatic hydrocarbon compound composition |  | Composition (1) | Composition (2) | Composition (3) |
| Composition of saturated aliphatic hydrocarbon compound composition | C20 | 0.5 | 0 | 0.5 |
|  | C30 | 1.5 | 0.6 | 0.5 |
|  | C40 | 94.6 | 98.8 | 98.8 |
|  | C50 | 1.2 | 0.4 | 0.1 |
|  | C60 | 2.2 | 0.2 | 0.1 |
|  | C70 | 0 | 0 | 0 |
|  | C80 | 0 | 0 | 0 |
|  | Average carbon number | 40.31 | 40.02 | 39.88 |
|  | C40 main peak area (%) | 23 | 88 | 53 |
| Properties of saturated aliphatic hydrocarbon compound composition | Evaporation loss (Noack method) (%) | 3.4 | 8.1 | 7.4 |
|  | 100° C. kinetic viscosity (mm²/s) | 5.86 | 6.07 | 5.88 |
|  | 40° C. kinetic viscosity (mm²/s) | 30.33 | 32.22 | 30.57 |
|  | Viscosity index | 140.6 | 138.0 | 139.8 |
|  | Cold cranking viscosity (CCS; −35° C.) (mPa · s) | 3350 | 3850 | 3300 |
|  | Pour point (° C.) | less than −50 | less than −50 | less than −50 |

The saturated aliphatic hydrocarbon compound composition, obtained in Example 1, has an evaporation loss of 4% by mass or less as determined by the Noack method, and a kinematic viscosity at 100° C. of 6.5 mm²/s or less. Therefore, the use of this composition as a base oil can provide a long-life lubricating oil.

Production Example 2 (Production of a Mixture of a Vinylidene Olefin Having a Carbon Number of 20 and an α-Olefin Having a Carbon Number of 10: A Mixture of a 1-Decene Dimer and 1-Decene)

1000 L of 1-decene was placed into a heated/dried reactor having an interior volume of 1500 L in a nitrogen atmosphere, and 1.33 L of 3 mol/L methylaluminoxane was added to the 1-decene, and the temperature of the mixture was raised to 35° C. Subsequently, 6.4 L of a 10 mmol/L toluene solution of bis(t-butylcyclopentadienyl)zirconium dichloride was added to the mixture, and the resulting mixture was reacted at 40° C. and a hydrogen pressure of 3 kPa (C) for 9 hours. The reaction was stopped with 200 L of a 1 mass % aqueous NaOH solution, and the reaction product was washed twice with ion-exchange water. Subsequently, the reaction product was distilled to remove a high-boiling fraction, thereby obtaining a mixture of a 1-decene dimer and 1-decene. The composition of the mixture was as follows: 78.7 mass % of 1-decene dimer and 21.3 mass % of 1-decene. The mixture of a 1-decene dimer and 1-decene, obtained in this production example, will be termed C20·C10 olefin (2) in the following Examples and Comparative Examples.

Example 2 (Production of Saturated Aliphatic Hydrocarbon Compound Composition (4))

A saturated aliphatic hydrocarbon compound composition (4) was produced in the same manner as in Example 1 except that in the production of the saturated aliphatic hydrocarbon compound composition (1) of Example 1, the C20·C10 olefin (2), obtained in Production Example 2, was used instead of the C20 olefin (1) obtained in Production Example 1 and used in the oligomerization step (step 1) (1), and the distillation conditions used in the distillation step (4) were changed to conditions suited for the saturated aliphatic hydrocarbon compound composition (4). Gas chromatographic analysis of the product revealed that the proportion of the main peak area was 16% of the total peak area corresponding to the component with a carbon number of 40. The composition and properties of the resulting composition are shown in Table 2 below.

Comparative Example 3 (Production of Saturated Aliphatic Hydrocarbon Compound Composition (5))

A saturated aliphatic hydrocarbon compound composition (5) having an average carbon number of 40 was produced in the same manner as in Example 2 except that in the production of the saturated aliphatic hydrocarbon compound composition (4) of Example 2, the isomerization step (step 2) (2) was not performed. Gas chromatographic analysis of the product revealed that the proportion of the main peak area was 80% of the total peak area corresponding to the component with a carbon number of 40. The composition and properties of the resulting composition are shown in Table 2 below.

TABLE 2

|  |  | Example 2 | Comp. Example 3 |
|---|---|---|---|
| Step 1 (oligomerization) | Olefin | C20•C10 olefin (2) | C20•C10 olefin (2) |
|  | Catalyst | t-BuCl/DEAC | t-BuCl/DEAC |
|  | Reaction temp. (° C.) | 30 | 30 |
| Step 2 (isomerization) | Catalyst | t-BuCl/DEAC | — |
|  | Reaction temp. (° C.) | 150 | — |
| Step 3 (hydrogenation) | Catalyst | Pd/alumina | Pd/alumina |
| Number of saturated aliphatic hydrocarbon compound composition |  | Composition (4) | Composition (5) |
| Composition of saturated aliphatic hydrocarbon compound composition | C20 | 0 | 0.8 |
|  | C30 | 20.4 | 12.9 |
|  | C40 | 69.4 | 70.1 |
|  | C50 | 8.5 | 6.2 |
|  | C60 | 1.7 | 8.2 |
|  | C70 | 0 | 1.1 |
|  | C80 | 0 | 0.8 |
|  | Average carbon number | 39.15 | 40.86 |
|  | C40 main peak area (%) | 16 | 80 |
| Properties of saturated aliphatic hydrocarbon compound composition | Evaporation loss (Noack method) (%) | 5.3 | 8.8 |
|  | 100° C. kinetic viscosity (mm²/s) | 5.57 | 6.48 |
|  | 40° C. kinetic viscosity (mm²/s) | 28.66 | 35.81 |
|  | Viscosity index | 136.1 | 136.7 |
|  | Cold cranking viscosity (CCS; −35° C.) (mPa · s) | 3350 | 4550 |
|  | pour point (° C.) | less than −50 | less than −50 |

The data clearly shows that compared to the production methods of the Comparative Examples, which produced the saturated aliphatic hydrocarbon compound compositions each having approximately the same average carbon number as those of the compositions of the Examples, the production methods of Examples 1 and 2 can produce a saturated aliphatic hydrocarbon compound composition which has a low kinematic viscosity and yet has a low evaporation loss. The data thus indicates that the saturated aliphatic hydrocarbon compound compositions, obtained in the Examples, can serve as an excellent lubricant base oil whose properties do not deteriorate over a long period of time when it is used in a lubricating oil for machines, for which a low viscosity is required.

Production Example 3 (Production of a Mixture of Vinylidene Olefins Having a Carbon Number of 16 to 24: Production of a Dimer of a Mixture of 1-Octene, 1-Decene and 1-Dodecene)

1-octene, 1-decene and 1-dodecene, each in an amount of 666 mL, were placed into a heated/dried, nitrogen-purged glass container having an interior volume of 2 L, and a toluene solution of methylaluminoxane (20 mmol in terms of aluminum), a hexane solution of diethylaluminum chloride (4 mmol in terms of aluminum) and a toluene solution of bis(cyclopentadienyl)zirconium dichloride (2 mmol) were sequentially added to the olefin mixture, and the resulting mixture was stirred at 50° C. 5 hours later, the reaction was stopped by adding an aqueous sodium hydroxide solution to the reaction mixture. Subsequently, the organic layer was subjected to vacuum distillation to obtain 1.1 L of a fraction (a mixture of vinylidene olefins having a carbon number of 16 to 24: a dimer of a mixture of 1-octene, 1-decene and 1-dodecene) with a boiling point of 115° C. to 180° C./24.0 Pa. Gas chromatographic analysis of the fraction revealed that the content of components having a carbon number of 16 to 24 was 96.5% by mass. The mixture of vinylidene olefins having a carbon number of 16 to 24, obtained in this production example, will be termed C16-24 olefin (3) in the following Examples and Comparative Examples.

Example 3 (Production of Saturated Aliphatic Hydrocarbon Compound Composition (6))

A saturated aliphatic hydrocarbon compound composition (6) whose main components have a carbon number of 32 to 48 was produced in the same manner as in Example 1 except that in the production of the saturated aliphatic hydrocarbon compound composition (1) of Example 1, the C16-24 olefin (3), obtained in Production Example 3, was used instead of the C20 olefin (1) obtained in Production Example 1 and used in the oligomerization step (step 1) (1), ethylaluminum sesquichloride (EASC) was used instead of diethylaluminum chloride (DEAC) in step 1 and step 2, and a fraction with a boiling point of 1%$^L$C/24.0 Pa or less was removed in the distillation step (4). The composition and properties of the resulting composition are shown in Table 3 below.

Comparative Example 4 (Production of Saturated Aliphatic Hydrocarbon Compound Composition (7))

A saturated aliphatic hydrocarbon compound composition (7) whose main components have a carbon number of 32 to 48 was produced in the same manner as in Example 3 except that in the production of the saturated aliphatic hydrocarbon compound composition (6) of Example 3, the isomerization step (step 2) (2) was not performed. The composition and properties of the resulting composition are shown in Table 3 below.

TABLE 3

|  |  | Example 3 | Comp. Example 4 |
|---|---|---|---|
| Step 1 (oligomerization) | Olefin | C16-C24 olefin (3) | C16-C24 olefin (3) |
|  | Catalyst | t-BuCl/EASC | t-BuCl/EASC |
|  | Reaction temp. (° C.) | 80 | 30 |
| Step 2 (isomerization) | Catalyst | t-BuCl/EASC | — |
|  | Reaction temp. (° C.) | 150 | — |
| Step 3 (hydrogenation) | Catalyst | Pd/alumina | Pd/alumina |
| Number of saturated aliphatic hydrocarbon compound composition |  | Composition (6) | Composition (7) |
| Composition of saturated aliphatic hydrocarbon compound composition | C30 or lower | 1.80 | 0.70 |
|  | C32 | 2.30 | 1.70 |
|  | C34 | 6.62 | 6.09 |
|  | C36 | 14.75 | 14.43 |
|  | C38 | 21.90 | 21.87 |
|  | C40 | 23.44 | 24.07 |
|  | C42 | 16.94 | 17.85 |
|  | C44 | 8.35 | 9.09 |
|  | C46 | 2.17 | 2.53 |
|  | C48 | 0.56 | 0.36 |
|  | C50 or higher | 1.20 | 1.30 |
|  | Average carbon number | 39.1 | 39.5 |
|  | C40 main peak area (%) | 39.2 | 85.1 |

TABLE 3-continued

|  |  | Example 3 | Comp. Example 4 |
|---|---|---|---|
| Properties of saturated aliphatic hydrocarbon compound composition | Evaporation loss (Noack method) (%) | 3.50 | 5.50 |
|  | 100° C. kinetic viscosity (mm²/s) | 6.16 | 6.26 |
|  | 40° C. kinetic viscosity (mm²/s) | 33.04 | 33.90 |
|  | Viscosity index | 137.1 | 136.0 |

The data clearly shows that compared to the production method of Comparative Example 4, which produced the saturated aliphatic hydrocarbon compound compositions having approximately the same average carbon number as that of the composition of Example 3, the production method of Examples 3 can produce a saturated aliphatic hydrocarbon compound composition which has a kinematic viscosity comparable to that of the comparative composition and has a very low evaporation loss. The data thus indicates that the saturated aliphatic hydrocarbon compound composition, obtained in Example 3, can serve as an excellent lubricant base oil whose properties do not deteriorate over a long period of time when it is used e.g. in a lubricating oil having an adjusted particular viscosity.

The invention claimed is:

1. A saturated aliphatic hydrocarbon compound composition, comprising:
   a saturated aliphatic hydrocarbon compound, having a carbon number of 40, in 20% by mass or more,
   wherein the saturated aliphatic hydrocarbon compound comprises a plurality of isomers, in a gas chromatography chromatogram of the saturated aliphatic hydrocarbon compound composition, an area of a main peak is 40% or less of a total peak area corresponding to the saturated aliphatic hydrocarbon compound, and the saturated aliphatic hydrocarbon compound composition has an evaporation loss of 4% by mass or less as determined by the Noack method, a kinematic viscosity at 100° C. of 6.5 mm²/s or less, and an average carbon number of 36 to 44.

2. The saturated aliphatic hydrocarbon compound composition of claim 1, wherein the plurality of isomers of the saturated aliphatic hydrocarbon compound are 90% by mass or more of the composition.

3. The saturated aliphatic hydrocarbon compound composition of claim 2, wherein the area of the main peak is 35% or less of the total peak area.

4. The saturated aliphatic hydrocarbon compound composition of claim 1, wherein the area of the main peak is 35% or less of the total peak area.

5. The saturated aliphatic hydrocarbon compound composition of claim 1, wherein the plurality of the isomers comprises 11-methyl-11,13-dioctyltricosane at a content of 40% by mass or less, relative to total isomer mass.

6. The saturated aliphatic hydrocarbon compound composition of claim 1, wherein a content of the saturated aliphatic hydrocarbon compound is 30% by mass or more.

7. The saturated aliphatic hydrocarbon compound composition of claim 1, wherein a content of the saturated aliphatic hydrocarbon compound is 90% by mass or more.

8. The saturated aliphatic hydrocarbon compound composition of claim 1, wherein a content of the saturated aliphatic hydrocarbon compound is 94% by mass or more.

9. The saturated aliphatic hydrocarbon compound composition of claim 1, wherein the saturated aliphatic hydrocarbon compound composition has a proportion of quaternary carbon atoms per molecule in 1.0% or less.

10. The saturated aliphatic hydrocarbon compound composition of claim 1, wherein the saturated aliphatic hydrocarbon compound comprises 11-methyl-11,13-dioctyltricosane in a content of 23% by mass or less.

11. The saturated aliphatic hydrocarbon compound composition of claim 1, wherein the area of the main peak is 25% or less of the total peak area.

12. A lubricating oil composition, comprising:
   the saturated aliphatic hydrocarbon compound composition of claim 1.

13. A method for producing the saturated aliphatic hydrocarbon compound composition of claim 1, comprising:
   oligomerizing an olefin to obtain an olefin oligomer;
   isomerizing the olefin oligomer to obtain an isomer; and
   hydrogenating the isomer to obtain the saturated aliphatic hydrocarbon compound composition.

14. The method of claim 13, wherein the olefin oligomer is isomerized in the presence of a Friedel-Crafts catalyst.

15. The method of claim 14, wherein the Friedel-Crafts catalyst comprises an organoaluminum compound.

16. The method of claim 13, wherein the olefin is oligomerized in the presence of a Friedel-Crafts catalyst.

17. The method of claim 13, further comprising:
   distilling the saturated aliphatic hydrocarbon compound composition.

18. The method of claim 13, wherein the olefin comprises 90% by mass or more of an olefin having a carbon number of 20.

19. The method of claim 13, wherein the olefin is a dimer of 1-decene.

* * * * *